United States Patent
Nowak

(10) Patent No.: US 10,478,868 B2
(45) Date of Patent: Nov. 19, 2019

(54) METHOD AND APPARATUS FOR SURFACE NANOPARTICLE MEASUREMENT

(71) Applicant: Applied Materials, Inc., Santa Clara, CA (US)

(72) Inventor: Thomas Nowak, Cupertino, CA (US)

(73) Assignee: APPLIED MATIERIALS, INC., Santa Clara, CA (US)

( * ) Notice: Subject to any disclaimer, the term of this patent is extended or adjusted under 35 U.S.C. 154(b) by 253 days.

(21) Appl. No.: 15/349,443

(22) Filed: Nov. 11, 2016

(65) Prior Publication Data

US 2017/0157651 A1 Jun. 8, 2017

Related U.S. Application Data

(60) Provisional application No. 62/263,507, filed on Dec. 4, 2015.

(51) Int. Cl.
*B08B 15/04* (2006.01)
*B08B 5/02* (2006.01)
*G01N 15/06* (2006.01)

(52) U.S. Cl.
CPC ........... *B08B 5/02* (2013.01); *B08B 15/04* (2013.01); *G01N 15/0618* (2013.01)

(58) Field of Classification Search
CPC ........ B08B 5/02; B08B 15/04; G01N 1/2205; G01N 15/0618; G01N 2015/1062; G01N 2015/1486; G01N 2001/2223; G01N 2001/028; G01N 1/2202; G01N 2015/0046
USPC ........................................................ 73/864
See application file for complete search history.

(56) References Cited

U.S. PATENT DOCUMENTS

| | | | |
|---|---|---|---|
| 4,205,728 A * | 6/1980 | Gloor | B23Q 11/0046 175/209 |
| 4,391,151 A * | 7/1983 | Nelson | G01N 1/2205 73/863.23 |
| 5,253,538 A | 10/1993 | Swick et al. | |

(Continued)

FOREIGN PATENT DOCUMENTS

JP 2016223918 A * 12/2016

OTHER PUBLICATIONS

Written Opinion and International Search Report for PCT/US2016/060238 dated Feb. 16, 2017.

(Continued)

*Primary Examiner* — Nimeshkumar D Patel
*Assistant Examiner* — Nashmiya S Fayyaz
(74) *Attorney, Agent, or Firm* — Patterson + Sheridan LLP

(57) ABSTRACT

Embodiments described herein generally relate to a particle collection apparatus and probe head for the collection of particles on process tool components. In one embodiment, a particle collection apparatus for counting particles present on a processing tool component is disclosed herein. The particle collection apparatus includes a particle collector. The particle collector is configured to scan a processing tool component and collect particles collected from the processing tool component. The particle collector includes a body and a probe head coupled to the body. The probe head has a probe body and a controlled spacing element. The controlled spacing element is coupled to the probe body and is configured to form a uniform manifold between the probe body and the processing tool component.

17 Claims, 9 Drawing Sheets

(56) References Cited

U.S. PATENT DOCUMENTS

| | | | | |
|---|---|---|---|---|
| 5,660,240 | A * | 8/1997 | Harms | B23Q 11/0046 |
| | | | | 175/209 |
| 5,983,445 | A * | 11/1999 | Baker | B08B 15/04 |
| | | | | 144/252.1 |
| 6,378,385 | B1 | 4/2002 | Bowers | |
| 6,898,991 | B2 * | 5/2005 | Geise | G01N 1/02 |
| | | | | 73/864.52 |
| 7,281,886 | B2 * | 10/2007 | Stoerig | B23Q 11/0046 |
| | | | | 175/213 |
| 2002/0083780 | A1 * | 7/2002 | Lutz | G01N 1/2205 |
| | | | | 73/863.01 |
| 2006/0123743 | A1 * | 6/2006 | Heer | B01D 53/0415 |
| | | | | 55/309 |
| 2006/0185520 | A1 | 8/2006 | Jordan et al. | |
| 2007/0107495 | A1 | 5/2007 | Kim et al. | |
| 2008/0236620 | A1 | 10/2008 | Shih et al. | |

OTHER PUBLICATIONS

The Wall Shear Stress Produced by the Normal Impingement of a Jet on a Flat Surface, D.J. Phares, et. al., J. Fluid Mech. (2000), vol. 418, pp. 351-375.

Measurements of Air Jet Removal Efficiencies of Spherical Particles from Cloth and Planar Surfaces, R. Fletcher et al., Aerosol Science and Technology, 42: 1052-1061, 2008.

Effect of Angle on Particle Deposition in an Impingement Jet, T.G. Walmsley et al., 17th Australasian Fluid Mechanics Conference, 2010, 4 pages.

Modified Kinetic Model of Particle Detachment by Aerodynamic Drag and Vibration, N. Tippayawong et al., Proceedings of the World Congress on Engineering and Computer Science, vol. II, WCECS 2010, San Francisco, USA.

Experimental humidity dependency of small particle adhesion on silica and titania, M. Paajanen et. al, Journal of Colloid and Interface Science 304, 518-523 (2006).

Experimental Investigation of Particle Removal from Surfaces by Pulsed Air Jets, G. Ziskind et al., Aerosol Science & Technology, 36: 652-659, 2002.

Removal of Fine powders from Film Surface I. Effect of Electrostatic Force on the Removal Efficiency, S. Watano, et al., Chem. Pharm. Bull. 50, 1258-1261 (2002).

Removal of Fine powders from Film Surface II. Effect of Operating Parameters on the Removal Efficiency, S. Watano, et al., Chem. Pharm. Bull. 50, 1262-1264 (2002).

Cleanroom Techniques to Improve Surface Cleanliness and Repeatability for SRF Coldmass Production, L. Popielarski, et al., Proceedings of IPAC2012, New Orleans, Louisiana, USA.

Optical Measurements of Surface Particles for Evaluating Removal Performance of Air-Jet, M.T. Hong et al., Aerosol Science & Technology, 23, 665-673 (2007).

J.P. Shi et al., Sources and Concentration of Nonparticles (<10 nm Diameter) in the Urban Atmosphere, Atmospheric Environment 35, 1193-1202 (2001).

ISO 14644-9 Classification of Surface Cleanliness by Particle Concentration.

Transport of Nanoparticles in Gases: Overview & Recent Advances, Mädler et al., Aerosol and Air Quality Research 7, 304-342, 2007.

Particle Resuspension in Turbulent Flow: A Stochastic Model for Individual Soil Grains, A.R. Harris et al., Aerosol Science and Technology, 42:613-628, 2008.

The Impingement of Sonic and Sub-Sonic Jets onto a Flat Plate at Inclined Angles, J.W. Crafton, PhD Thesis, Purdue University, 2004.

Experimental Study of Microparticle Adhesion and Resuspension with Laser Doppler Vibrometry, J. A. Hubbard, Sandia Report, SAND2012-7206, Sep. 2012.

The Particle Cleanliness Validation System, I.F. Stowers et al., 2002, 48th Annual Technical Meeting of the Institute of Environmental Sciences and Technology, Anaheim, CA, Apr. 28-May 1, 2002.

O.R. Walton, Review of Adhesion Fundamentals for Micron-Scale Particles, KONA Powder and Particle Journal No. 26, 2008.

Simulation of the Adhesion of Particles to Surface. K. Cooper et al., Journal of Colloid and Interface Science 234, 284-292 (2001).

Accelerating the Next Technology Revolution, Sematech, 2012.

Adhesion as an Interplay Between Particle Size and Surface Roughness, Katainen et al., Journal of Colloid and Interface Science, 2006, 524-529.

QIII Ultra Surface Particle Detector, Pentagon Technologies, <http://www.pen-tec.com/products/qiii-ultra>, retrieved Jun. 25, 2019.

Solair 3100 Portable Particle Counter, Lighthouse Worldwide Solutions, <https://www.golighthouse.com/en/airborne-particle-counters/solair-3100>, retrieved Jun. 25, 2019.

Abound Vortex Surface Impingement Method for Adhered Dust Particle Removal, N. M. Vachon, M.S. Thesis, University of Vermont, 2010.

Wafersense Airborne Particle Sensor , Cyber Optics, https:-//cyberoptics.com/semiconductor/wafersense-airborne-particle-sensor-aps-2/ <https://cyberoptics.com/semiconductor/wafersense-airborne-particle-sensor-aps-2/>, retrieved Jun. 25, 2019.

Kumar et al., Scaling of the Adhesion between Particles and Surfaces from Micron-Scale to the Nanometer Scale, Purdue paper.

* cited by examiner

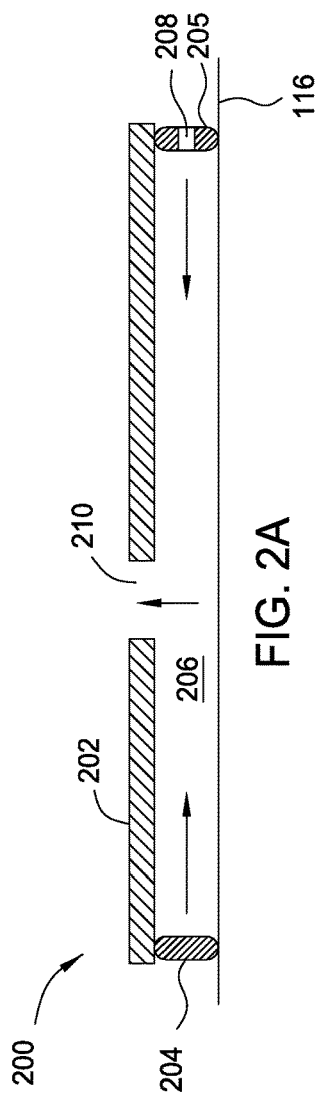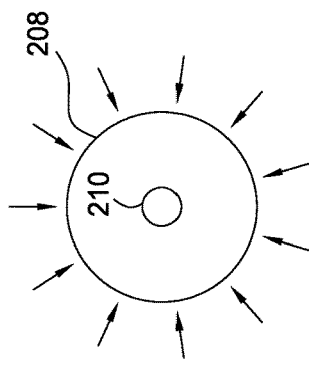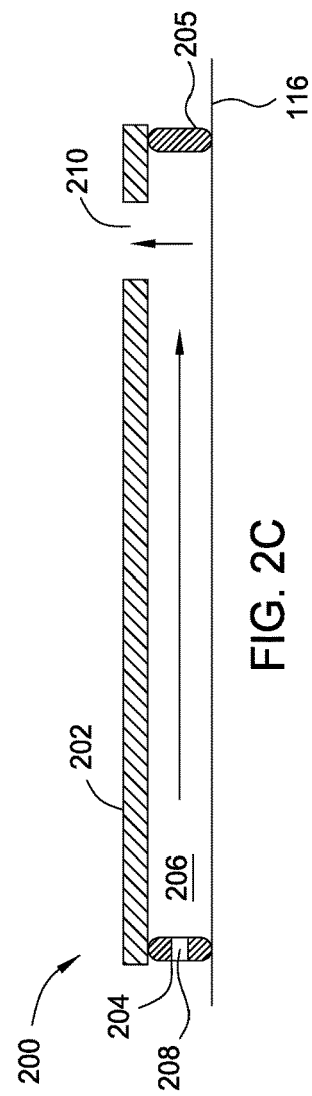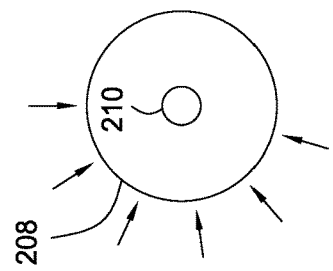

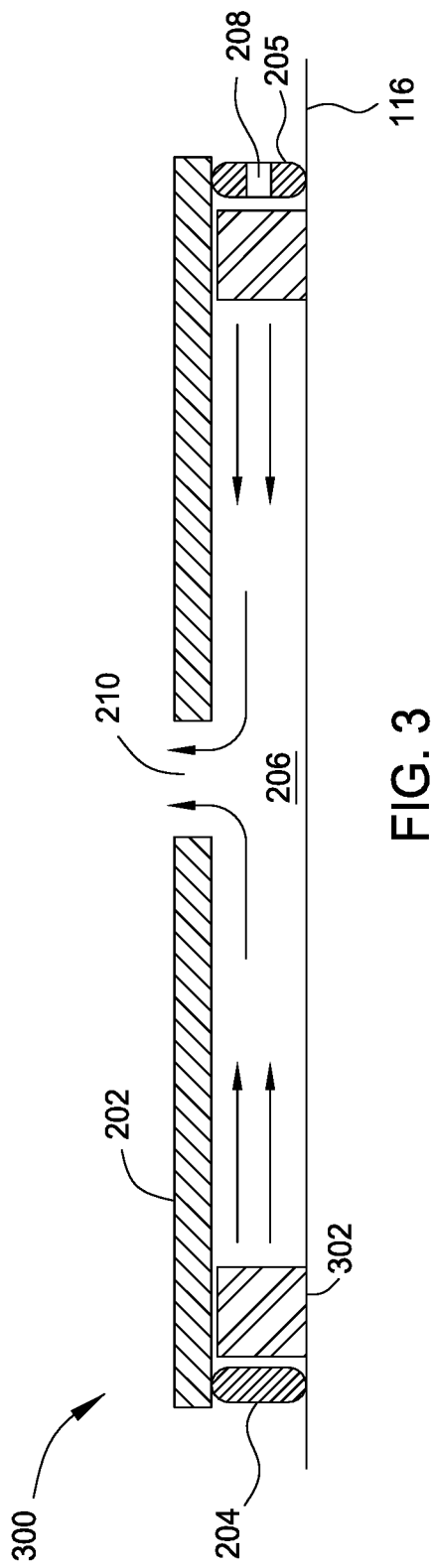
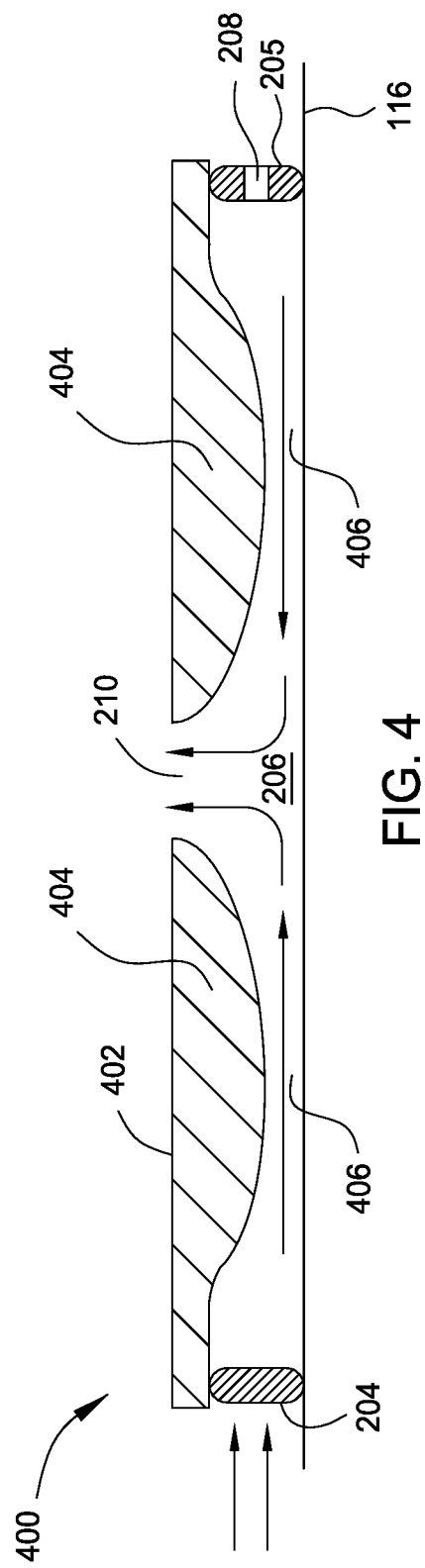

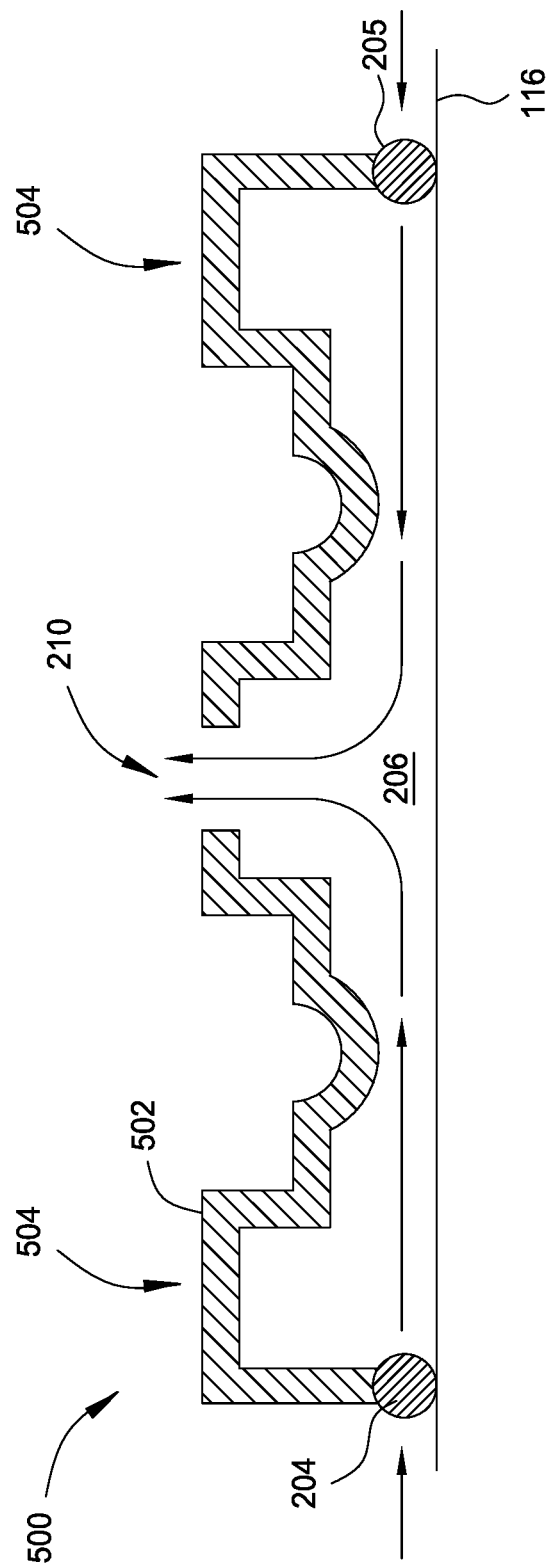

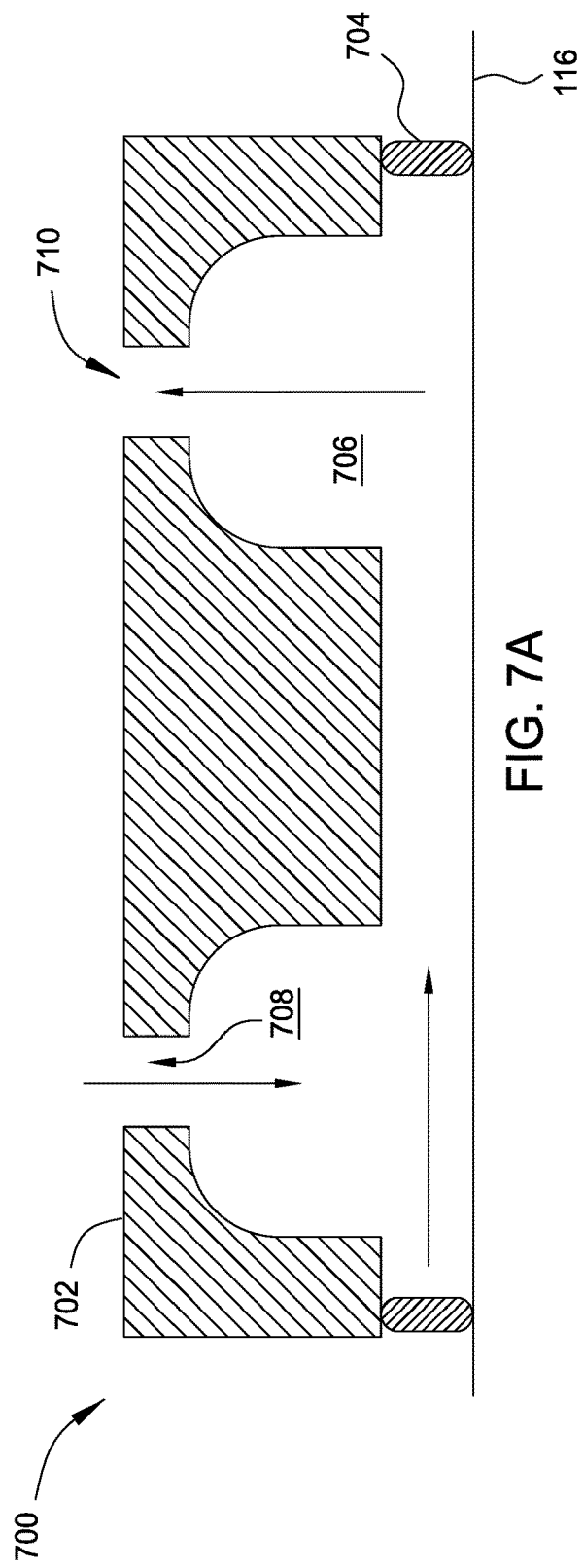

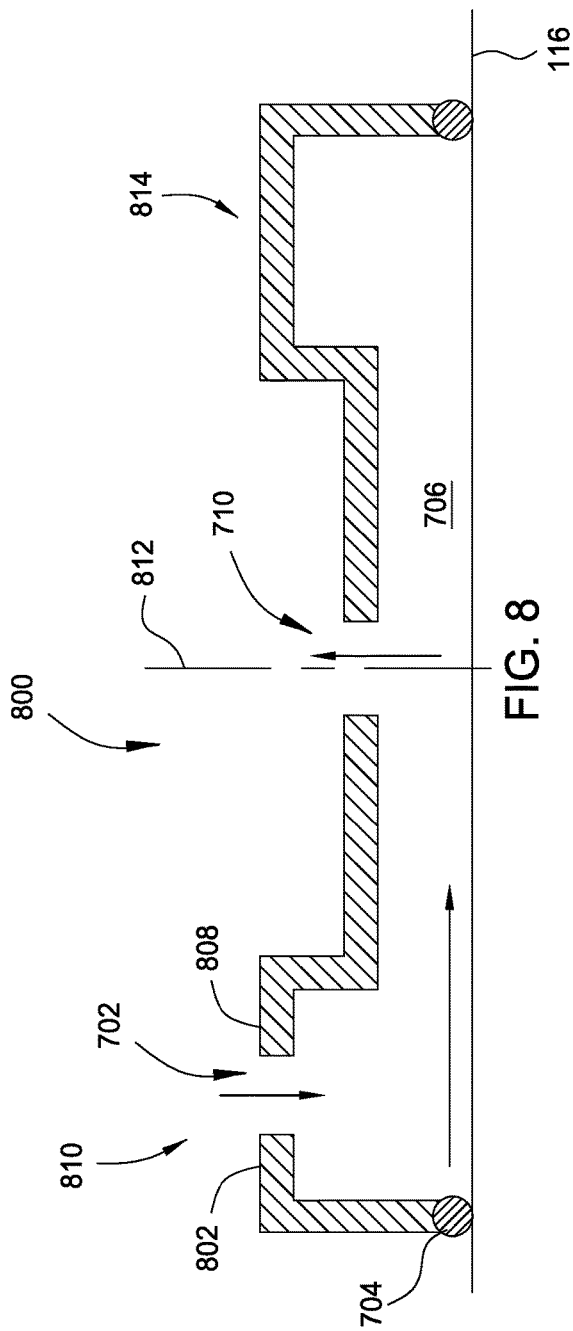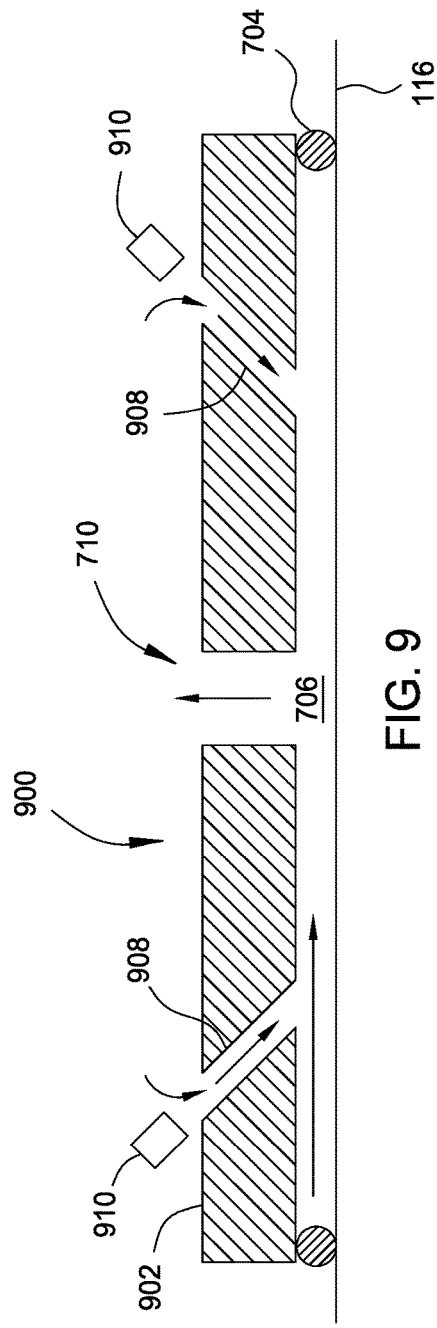

METHOD AND APPARATUS FOR SURFACE NANOPARTICLE MEASUREMENT

CROSS-REFERENCE TO RELATED APPLICATIONS

This application claims priority from U.S. Provisional Application Ser. No. 62/263,507 filed Dec. 4, 2015, which is hereby incorporated by reference in its entirety.

BACKGROUND

Field

Embodiments described herein relate to cleanliness control of process tool components, and more specifically to a particle collection apparatus and probe head for the collection of particles on process tool components.

Description of the Related Art

Substrate processing tool cleanliness "out of the box" is becoming an increasingly important issue during tool start-up. To consistently deliver clean tools, it is helpful to control cleanliness of substrate processing tools at the component and subsystem levels throughout the various stages of manufacturing and assembly. To control cleanliness, it is helpful to be able to measure cleanliness of the substrate processing tools at the desired particle sizes.

Substrate processing tools often involved complex geometries. The issue of measuring particle concentration on components of various materials and potentially complex geometry is different from the issue of measuring and characterizing particle levels on essentially planar substrates. Although metrology tools capable of detecting particles in the size range of 26 nm and below are available for substrates, and particles smaller than 26 nm can be imaged and measured on small samples that are capable of being placed in a scanning electron microscope (SEM), there are no commercial or high-volume manufacturing-worthy products available to measure particle concentration in the desired size range on the majority of the components that make up the substrate processing tools. Leading semiconductor industry roadmaps project critical defect size as half design rule critical dimensions (e.g., critical defect size of 10 nm for 20 nm node, and 5 nm critical defect size for 10 nm nodes). Current state of the art in surface particle metrology for substrate processing tool components (as opposed to substrates) is limited to particle sizes greater than or equal to 100 nm. In order to ensure the appropriate cleanliness of the substrate processing environment, all component surfaces in the substrate processing tool must be maintained at a certain level of cleanliness. This requirement extends throughout the entire tool manufacturing process.

Therefore, there is a need for devices and methods for improved particle detection on substrate processing tool components.

SUMMARY

Embodiments described herein generally relate to a particle collection apparatus and probe head for the collection of particles on process tool components. In one embodiment, a particle collection apparatus for counting particles present on a processing tool component is disclosed herein. The particle collection apparatus includes a particle collector. The particle collector is configured to scan the processing tool component and collect particles collected from a processing tool component. The particle collector includes a body and a probe head coupled to the body. The probe head has a probe body and a controlled spacing element. The controlled spacing element is coupled to the probe body and is configured to form a uniform manifold between the probe body and the processing tool component.

In another embodiment, a particle collecting apparatus is disclosed herein. The particle collecting apparatus includes a body, a probe head coupled to the body, and a counter. The probe head has a probe body and a controlled spacing element. The controlled spacing element is coupled to the probe body and is configured to form a uniform manifold between the probe body and the processing tool component. The counter configured to collect particles from a surface of a processing tool component In another embodiment, a method of collecting particles from a surface of a processing tool component is disclosed herein. The method includes maintaining a constant volume between a particle collector and the processing tool component, providing gas to a surface of the processing tool component, dislodging particles from the processing tool component, collecting the dislodged particles from the processing tool component, and counting the dislodged particles.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIG. 2A illustrates a probe head for use in the clean room environment of FIG. 1, according to one embodiment.

FIG. 2B illustrate a top view of the probe head of FIG. 2A.

FIG. 2C illustrates a probe head for use in the clean room environment of FIG. 1, according to one embodiment.

FIG. 2D illustrates a top view of the probe head of FIG. 2C.

FIG. 3 illustrates a probe head for use in the clean room environment of FIG. 1, according to one embodiment.

FIG. 4 illustrates a probe head for use in the clean room environment of FIG. 1, according to one embodiment.

FIG. 5 illustrates a probe head for use in the clean room environment of FIG. 1, according to one embodiment.

FIG. 7A illustrates a probe head for use in the clean room environment of FIG. 6, according to one embodiment.

FIG. 8 illustrates a probe head for use in the clean room environment of FIG. 6, according to one embodiment.

FIG. 9 illustrates a probe head for use in the clean room environment of FIG. 6, according to one embodiment.

For clarity, identical reference numerals have been used, where applicable, to designate identical elements that are common between figures. Additionally, elements of one embodiment may be advantageously adapted for utilization in other embodiments described herein.

DETAILED DESCRIPTION

Figure 1:
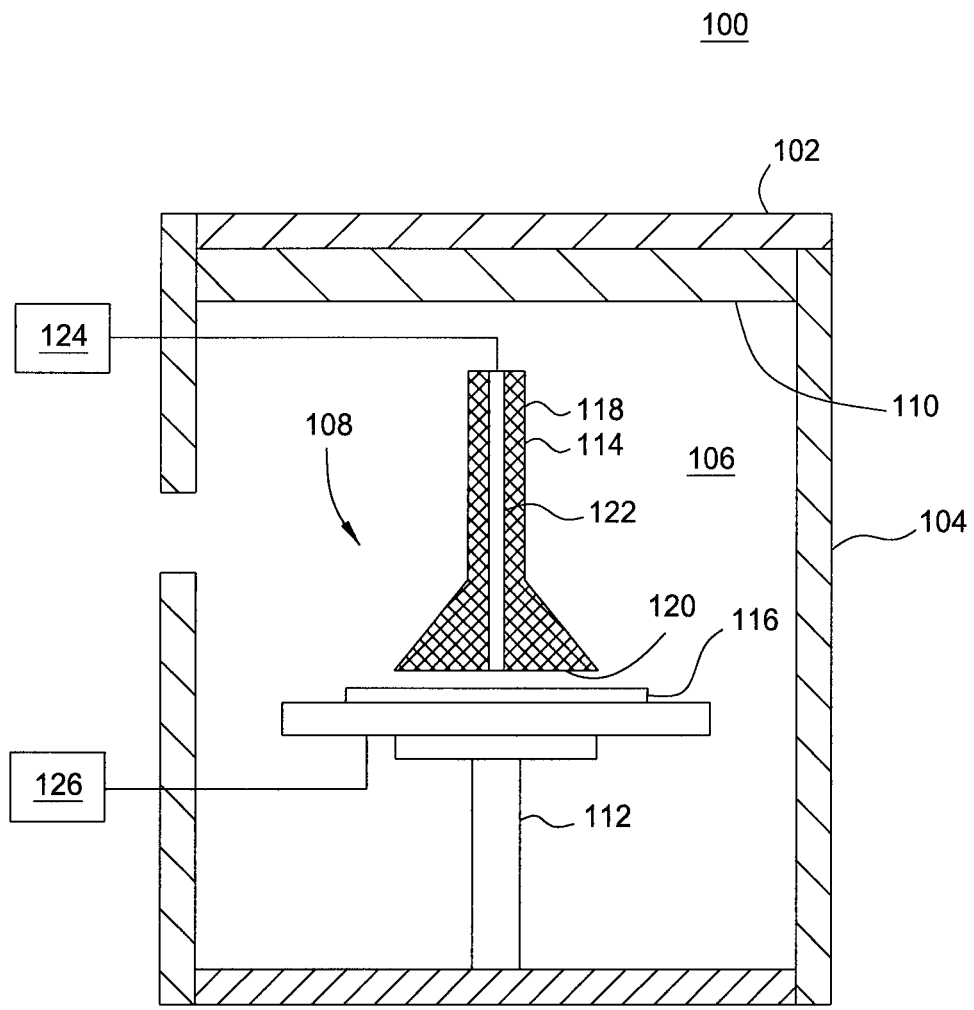
FIG. 1 illustrates a clean room environment for particle detection of processing tool component parts, according to one embodiment.

FIG. 1 illustrates a clean room environment 100 for detecting particles on processing tool component parts, according to one embodiment. The clean room environment 100 includes a chamber 102 having a chamber body 104 defining an interior volume 106 of the chamber 102. The chamber 102 includes a particle collection apparatus 108 and gas filter 110. The gas filter 110 is configured to reduce the number of particles in the clean room environment 100.

The particle collection apparatus 108 is configured to detect particles on processing tool component parts. The particle collection apparatus 108 includes a test bench 112 and a particle collector 114. The test bench 112 is configured to support a processing tool component 116, while a user scans the processing tool component 116 with the particle collector 114 to collect particles from the surface of the processing tool component 116. The particle collection apparatus is capable of collecting particles in the single-nanometer scale. For example, the particle collection apparatus may be capable of collecting particles having sizes from 1-2.5 nm.

The particle collector 114 includes a body 118 and a probe head 120. The probe head 120 is configured to be placed on the surface of the processing tool component 116. The probe head 120 is hollow and forms a uniform manifold between the probe head 120 and the processing tool component 116 when scanning the processing tool component. The uniform manifold minimizes the chances of user error by maintaining a constant volume between the probe head 120 and the processing tool component 116. If the volume changes while scanning, particles may be flushed into or out of the probe head 120, which will lead to poor test results. An exhaust conduit 122 is formed through the body 118 of the particle collection apparatus 108 and extends to the probe head 120. The exhaust conduit 122 is coupled to a particle counter 124. The particle counter 124 is configured to pump the particles from the particle collection apparatus 108 and count the number of particles collected. Because the probe head 120 is able to collect particles at sizes of a single-nanometer scale, the particle counter 124 can provide a more accurate reading of the cleanliness of the processing tool components.

In one embodiment, the particle collection apparatus 108 further includes a power source 126 coupled to the test bench 112. The power source 126 is configured to provide a voltage to the test bench 112 to generate an electric field about the processing tool component 116. Generating the electric field excites the particles on the surface of the processing tool component 116. Exciting the particles separates the particles from the bench 112, and allows the probe head 120 to more easily collect the particles.

FIG. 2 illustrates one embodiment of a probe head 200. The probe head 200 includes a probe body 202 and a controlled spacing element 204 coupled to the probe body 202. The controlled spacing element 204 forms a manifold 206 between the processing tool component 116 and the probe body 202. The controlled spacing element 204 ensures that the manifold 206 formed between the processing tool component 116 and the probe body 202 is uniform throughout the collection process. The uniform manifold 206 provides consistent flow conditions that lead to a more accurate particle collection process. In the embodiment illustrated in FIG. 2, the controlled spacing element 204 is a filter ring 205. The filter ring 205 allows ambient gas in the clean room environment 100 to be pulled into the manifold 206 by the particle counter 124 to separate the particles from the processing tool component 116. The gas may be pumped into the manifold 206 at a speed sufficient to separate the particles from the surface of the processing tool component 116. In one embodiment, a turbulent flow of gas is created in the manifold 206. In another embodiment, gas is pumped through the manifold 206 at a sonic speed.

FIG. 2B illustrates a top view of the probe head 200. The filter ring 205 includes a plurality of holes 208 distributed along the circumference of the filter ring 205. In one embodiment, the plurality of holes 208 is distributed uniformly around the circumference of the filter ring 205 such that incoming gas is distributed uniformly around the circumference. In another embodiment, the plurality of holes 208 is distributed asymmetrically around the circumference of the filter ring 205 to create a turbulent gas flow. In one embodiment, each hole 208 in the filter ring 205 has its own respective filter. In another embodiment, the holes may be angled to create a swirl of gas (i.e., turbulence) in the manifold 206. The gas is used to detach the particles from the surface of the processing tool component 116 such that the particles are more easily exhausted to the particle counter 124. The implementation of the filter ring 205 as the controlled spacing element also allows the gas entering the manifold 206 to be re-circulated. Recirculating the gas decreases the filter load because the filtered gas is making multiple trips through the filter ring 205.

The probe head 200 further includes an opening 210 formed about a center of the probe body 202. Forming the opening 210 about the center of the probe body 202 allows gas to enter the manifold 206 and exit the manifold 206 uniformly through the opening 210. In another embodiment, such as that shown in FIG. 2C, an opening 210' is formed at a position offset from the center of the probe body 202. The offset positioning of the opening 210' is implemented with an asymmetrical hole distribution in the filter ring 205. FIG. 2D illustrates the gas flow using the offset opening 210' illustrated in FIG. 2C.

FIG. 3 illustrates another embodiment of the probe head 300. The probe head 300 may further include an ionizer mesh ring disposed 302 disposed in the manifold 206. The ionizer mesh ring 302 is configured to neutralize the particles on the processing tool component 116 so that the exhaust conduit 122 can more easily pull the particles from the surface of the processing tool component 116.

FIG. 4 illustrates another embodiment of the probe head 400. The probe head 400 includes a probe body 402. The probe body 402 is substantially similar to the probe body 202. The probe body 402 includes an extended section 404. The extended section 404 extends farther into the manifold 206 compared to the remainder of the probe body 402, thus creating a smaller volume in the manifold 206 directly beneath the extended section 404. The change in volume in the manifold 206 creates a sonic throat 406 in the manifold. The sonic throat 406 increases the speed at which the gas flows through the manifold 206, thus creating a sonic flow. The increased flow leads to a greater particle separation potential. The greater particle separation potential leads to a greater particle collection potential, and thus more accurate tests.

FIG. 5 illustrates the probe head 500, according to another embodiment. The probe head 500 includes a probe body 502 and the filter ring 205. The filter ring 205 is coupled to the probe body 502. The probe body 502 includes a reservoir ring 504 formed therein. The reservoir ring 504 is configured to increase the volume of the manifold 206 formed between the component part and the probe body 502. Increasing the volume of the manifold 206 slows down the rate at which the particles exit through the opening 210, into the conduit 122, because the reservoir ring 504 collects dislodged particles in the increased volume. This allows the collection rate of the particle collector to match to rate at which the particle counter counts the particles, thus providing a more accurate reading. In one embodiment, the probe body 502 may also include an extended section, positioned between the reservoir ring 504 and the opening 210, to form a sonic throat such as that formed by extended section 404 in FIG. 4.

Figure 6:
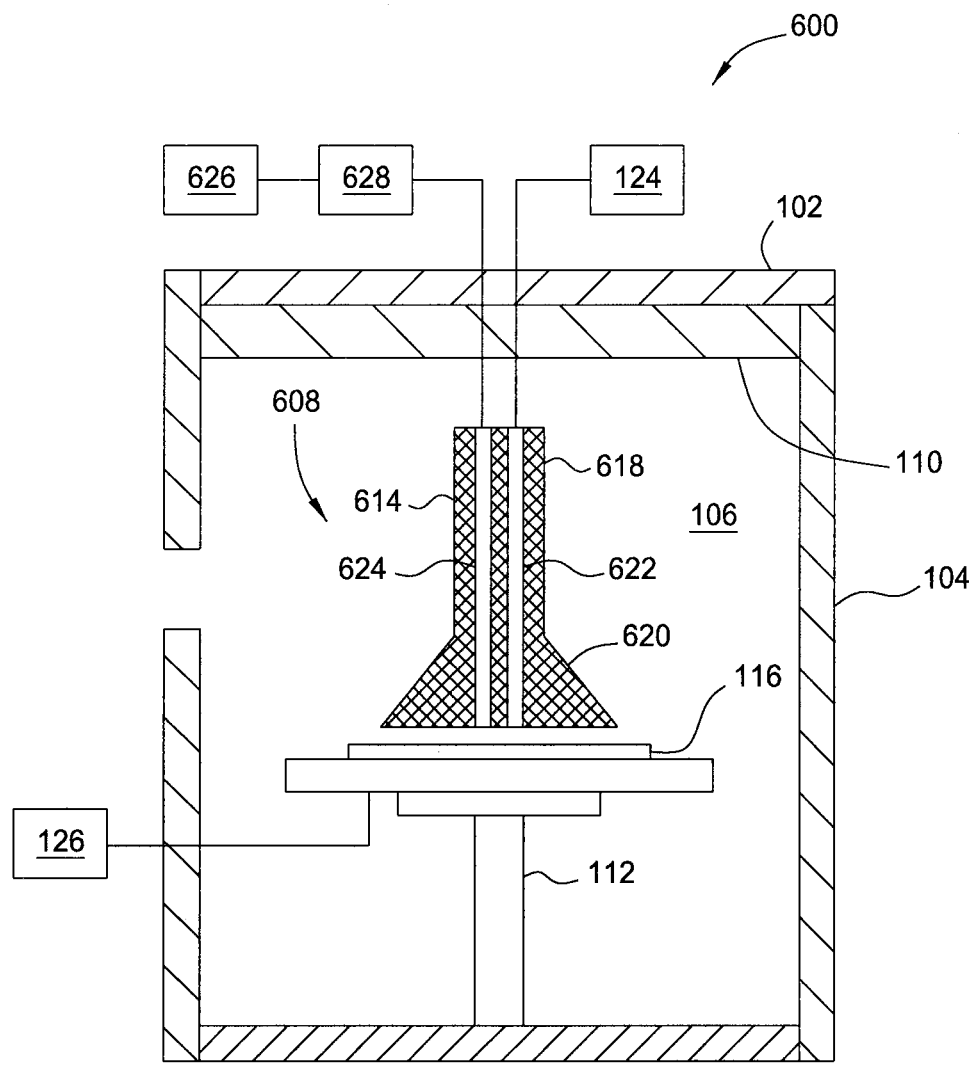
FIG. 6 illustrates a clean room environment for particle detection of processing tool component parts, according to one embodiment.

FIG. 6 illustrates a clean room environment 600 for particle detection of processing tool component parts, according to another embodiment. The clean room environment 600 is substantially similar to clean room environment 100. The clean room environment 600 includes a particle collection apparatus 608. The particle collection apparatus 608 is configured to detect particles on processing tool components.

The particle collection apparatus 608 includes the test bench 112 and a particle collector 614. The particle collector 614 is configured to scan the surface of the processing tool component 116 and collect any particles that may be present on its surface. The particle collector 614 is capable of collecting particles in the single-nanometer scale. The particle collector 614 includes a body 618 and a probe head 620. The probe head 620 is configured to be placed on the surface of the processing tool component 116. The probe head 620 forms a uniform manifold between the probe head 620 and the processing tool component 116 when scanning the processing tool component 116.

An exhaust conduit 622 is formed through the body 618 of the particle collector 614 and extends to the probe head 620. The exhaust conduit 622 is coupled to the particle counter 124. The particle counter 124 is configured to pump the particles from the particle collection apparatus 108 and count the number of particles collected. Because the probe head 620 is able to collect particles having sizes in the single-nanometer scale, the particle counter 124 can provide a more accurate reading of the cleanliness of the processing tool components 116. A gas inlet 624 is formed through the body 618 of the particle collector 614 and extends to the probe head 620. The gas inlet 624 is configured to provide gas to the surface of the processing tool component 116 to separate the particles from the processing tool component 116. In one embodiment, the gas inlet 624 is parallel to the exhaust conduit 622. In another embodiment, the gas inlet 624 is angled with respect to the exhaust conduit 622. The gas inlet 624 is coupled to a gas source 626. The gas source 626 may provide a gas such as air, nitrogen, or other clean gas. A filter 628 may be positioned between the gas source 626 and the gas inlet 624 to filter the gas entering the gas inlet 624. In one embodiment, the gas may be provided to the surface of the processing tool component 116 at a steady rate. In another embodiment, the gas may be provided to the surface of the processing tool component 116 at a pulsed rate.

In another embodiment, the gas inlet 624 may be used to provide a fluid to the surface of the processing tool component 116. The fluid is used to separate the particles from the processing tool component for collection. In this embodiment, a drying module (not shown) is used to quickly dry the processing tool component 116.

FIG. 7A illustrates a probe head 700 for use in particle collection apparatus 608, according to one embodiment. The probe head 700 includes a probe body 702 and a controlled spacing element 704. The controlled spacing element 704 is coupled to the probe body 702. The controlled spacing element 704 forms a manifold 706 between the processing tool component 116 and the probe body 702. The controlled spacing element 704 ensures that the manifold 706, formed between the processing tool component 116 and the probe body 702, is uniform throughout the collection process. The uniform manifold 706 provides consistent flow conditions that lead to a more efficient particle collection. In the embodiment illustrated in FIG. 7, the controlled spacing element 704 is a seal, such as a gasket or an o-ring. The controlled spacing element 704 is configured to prevent gas from escaping the manifold 706 and ambient gas from entering the manifold 706.

Figure 7B:
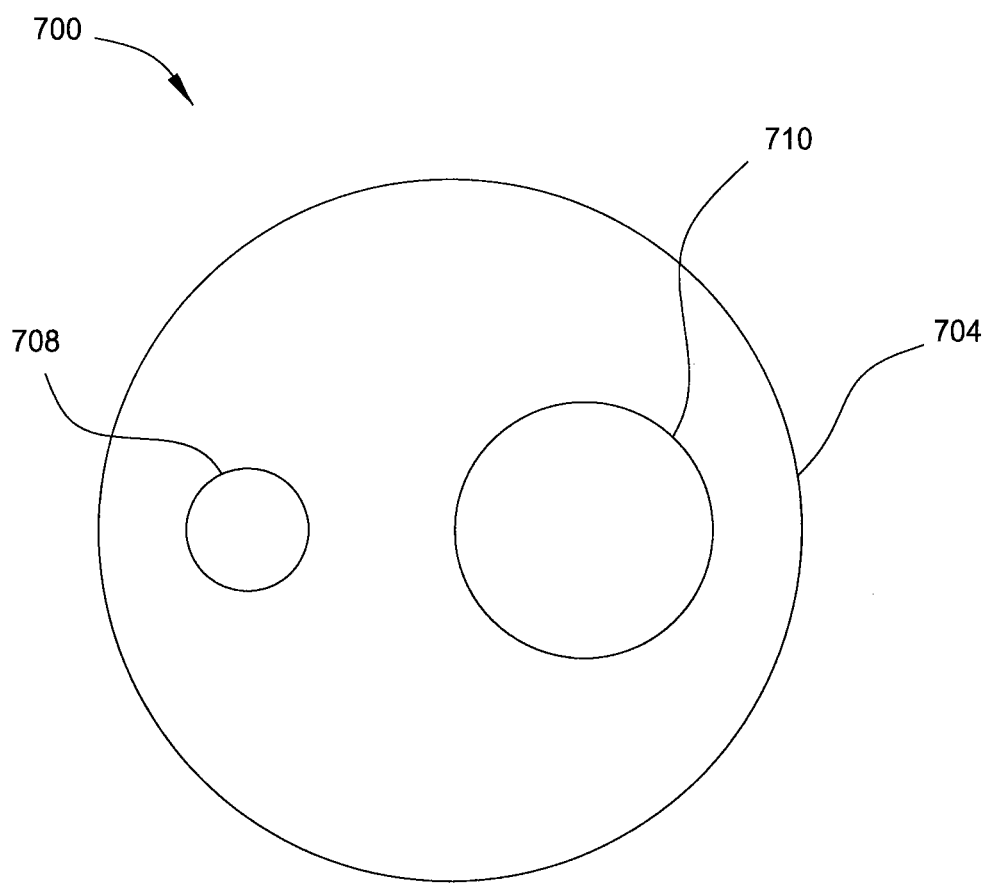
FIG. 7B illustrates a top view of the probe head of FIG. 7A.

FIG. 7B illustrates a top view of the probe head 700. The probe body 702 further includes a gas inlet 708 and a particle outlet 710. The gas inlet 708 is in communication with the gas inlet 624. In one embodiment, the gas inlet 708 may be substantially perpendicular to the surface of the processing tool component 116. In another embodiment, the gas inlet 708 may be angled with respect to the surface of the component part. For example, the gas inlet 708 may be formed at an angle of about 30° with respect to the surface of the processing tool component 116. Angling the gas inlet 708 allows for a more efficient removal of particles from the processing tool component 116 due to the angle at which the gas contacts the particles. The particle outlet 710 is in communication with the exhaust conduit 622. The particle outlet 710 is configured to receive particles for collection.

FIG. 8 illustrates one embodiment of a probe head 800 for use in particle collection apparatus 608. The probe head 800 includes a probe body 802 and the controlled spacing element 704. The probe body 802 includes a reservoir ring 808 formed therein. The reservoir ring 808 is similar to the reservoir ring 504 in FIG. 5. The gas inlet 708 is formed in the reservoir ring 808 at a first side 810 of a centerline 812 of the probe head 700, and the particle outlet 710 is formed in the reservoir ring at a second side 814 of the centerline. This allows the gas entering the manifold 706 to sweep across the manifold 706 from the first side 810 to the second side 814. In one embodiment, the probe body 802 may further include an extended member, similar to extended section 404 in FIG. 4, between the reservoir ring 808 and the particle outlet 710. The extended member forms a sonic throat in the manifold 706.

FIG. 9 illustrates a probe head 900, according to another embodiment. The probe head 900 includes a probe body 902 and the controlled spacing element 704. A plurality of angled gas inlets 908 is formed through the probe body 902 and open into the manifold 706. The angled gas inlets 908 may be formed at an angle less than 90 degrees with respect to the test bench. In one embodiment, the angled gas inlets 908 are coupled to the gas inlet 624. In another embodiment, the angled gas inlets 908 may be coupled to a syringe 910, configured to provide gas to the angled gas inlets. In one embodiment, the syringe may provide a steady stream of gas to the manifold 706. In another embodiment, the syringe 910 may provide a pulsed jet of gas to the manifold 706.

Figure 10:
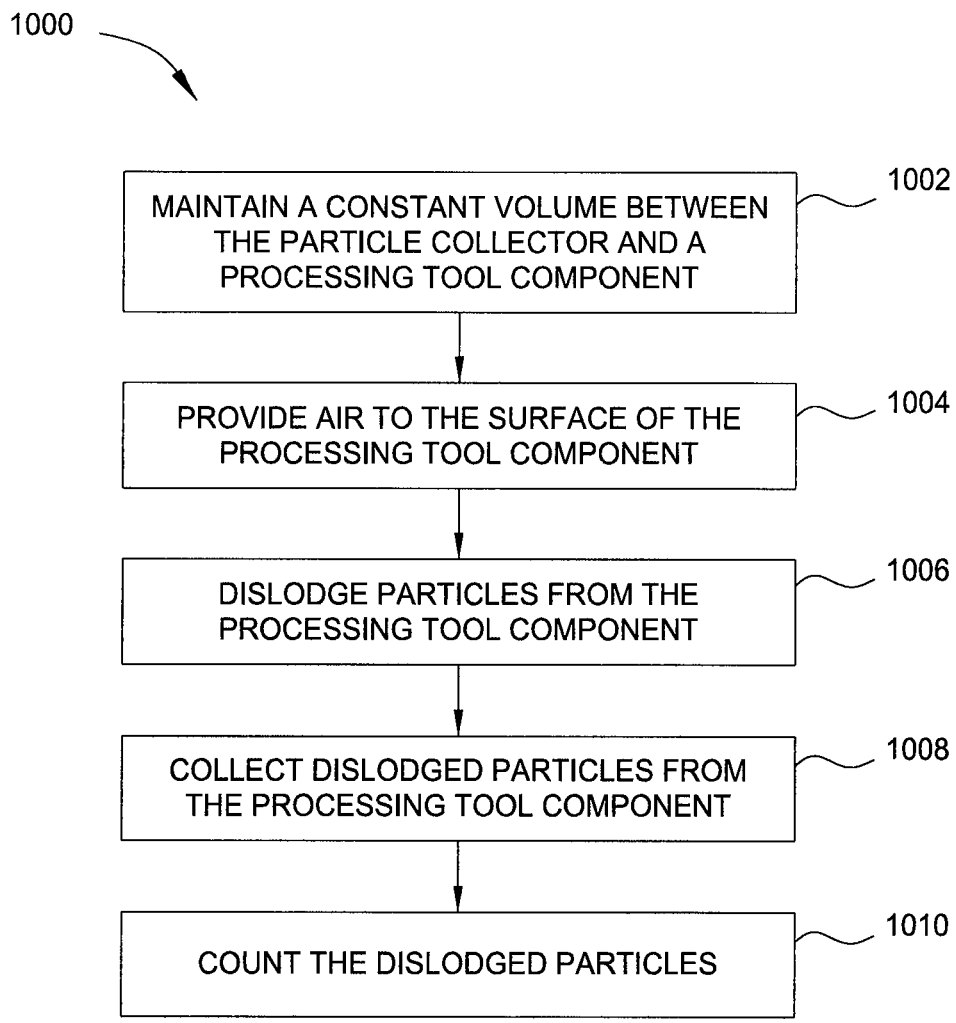
FIG. 10 illustrates a method of collecting particles from a surface of a processing tool component, according to one embodiment.

FIG. 10 illustrates a method 1000 of collecting particles from a surface of a processing tool component, according to one embodiment. The method 1000 begins at block 1002. At block 1002, a constant volume between the particle collector and the processing tool component is maintained once established. The constant volume is maintained through the use of a controlled spacing element, such as controlled spacing element 204 in FIGS. 2 and 704 in FIG. 7. In one embodiment, the controlled spacing element is a filter ring. In another embodiment, the controlled spacing element is an o-ring.

At block 1004, gas or other fluid is provided to the surface of the processing tool component. In one embodiment, the gas may be pumped in through a filter ring coupled to a probe body of the probe head. In another embodiment, the gas may be provided through a gas inlet formed in the probe body of the particle collector.

At block 1006, the particles are dislodged from the surface of the processing tool component. The gas provided to the surface of the processing tool component dislodges the particles. In one embodiment, a turbulent flow of gas dislodges the particles. In another embodiment, a pulsed flow of gas dislodges the particles. Dislodging the particles allows the particle collector to collect a greater number of particles from the surface of the processing tool. This is because the gas flow may dislodge particles as small as 1-2.5 nm, allowing the particle collector to collect particles of sizes not sampled by previous particle collecting techniques.

At block 1008, the particle collector collects the particles for the particle counter. The particle collector collects particles dislodged from the surface of the processing tool component. The collected particles are provided to the particle counter for counting the number of particles present on the processing tool component.

At block 1010, the particle counter counts the number of particles collected. Knowing the number of particles collected allows the user to know the number of defects present on the substrate. This allows the user to produce substrates that are within the industry standard.

While the foregoing is directed to specific embodiments, other and further embodiments may be devised without departing from the basic scope thereof, and the scope thereof is determined by the claims that follow.

What is claimed is:

1. A particle collection apparatus for counting particles present on a processing tool component, the apparatus comprising:
   a particle collector configured to collect particles from the processing tool component, the particle collector comprising:
      a body;
      a probe head coupled to the body, the probe head having a probe body and a controlled spacing element, wherein the controlled spacing element is coupled to the probe body and is configured to form a manifold between the probe body and the processing tool component, wherein the controlled spacing element is a filter ring; and
      an ionizer mesh ring disposed in the manifold.

2. The particle collection apparatus of claim 1, wherein the probe body includes an extended section configured to decrease a volume in the manifold at positions beneath the extended section.

3. The particle collection apparatus of claim 1, wherein the probe body includes a reservoir ring.

4. The particle collection apparatus of claim 1, wherein a gas inlet is formed through the probe body.

5. The particle collection apparatus of claim 4, wherein the probe body includes a reservoir ring.

6. The particle collection apparatus of claim 1, further comprising:
   a test bench, wherein the particle collector is disposed over the test bench; and
   a power source coupled to the test bench, the power source configured to excite particles from a surface of the processing tool component.

7. The particle collection apparatus of claim 1, further comprising:
   a counter configured to collect particles from a surface of the processing tool component.

8. The particle collection apparatus of claim 7, wherein the probe body includes an extended section configured to decrease a volume in the manifold at positions beneath the extended section.

9. The particle collection apparatus of claim 7, wherein the probe body includes a reservoir ring.

10. The particle collection apparatus of claim 1, wherein the manifold further comprises:
    a sonic throat.

11. The particle collection apparatus of claim 7, wherein a gas inlet is formed through the probe body.

12. A particle collection apparatus for counting particles present on a processing tool component, the apparatus comprising:
    a particle collector configured to collect particles from the processing tool component, the particle collector comprising:
       a body;
       a probe head coupled to the body, the probe head having a probe body and a controlled spacing element, wherein the controlled spacing element is coupled to the probe body and is configured to form a manifold between the probe body and the processing tool component, wherein the controlled spacing element is a filter ring having a plurality of holes, and wherein the plurality of holes are distributed asymmetrically around the circumference of the filter ring to create a turbulent gas flow; and
       an ionizer mesh ring disposed in the manifold; and
    a counter configured to count particles from a surface of the processing tool component.

13. The particle collection apparatus of claim 12, wherein the probe body includes an extended section configured to decrease a volume in the manifold at positions beneath the extended section.

14. The particle collection apparatus of claim 12, wherein an exhaust conduit is formed through the body and extends to the probe head, and the exhaust conduit is coupled to the counter.

15. The particle collection apparatus of claim 14, wherein the counter is configured to pump the particles from the particle collector and count the number of particles collected.

16. A particle collection apparatus for counting particles present on a processing tool component, the apparatus comprising:
    a particle collector configured collect particles from the processing tool component, the particle collector comprising:
       a body; and
       a probe head coupled to the body, the probe head having a probe body and a controlled spacing element, wherein the controlled spacing element is coupled to the probe body and is configured to form a manifold between the probe body and the processing tool component, wherein the controlled spacing element is a filter ring; and
       an ionizer mesh ring disposed in the manifold;
    a counter configured to collect particles from a surface of the processing tool component;

a test bench, wherein the particle collector is disposed over the test bench; and a power source coupled to the test bench, the power source configured to excite particles from the surface of the processing tool component.

17. The particle collection apparatus of claim 16, wherein an exhaust conduit is formed through the body and extends to the probe head, and the exhaust conduit is coupled to the counter.

* * * * *